(12) United States Patent
Ueda et al.

(10) Patent No.: US 12,398,417 B2
(45) Date of Patent: Aug. 26, 2025

(54) NUCLEIC ACID SEPARATION METHOD, DETECTION METHOD, NUCLEIC ACID PURIFICATION COLUMN AND METHOD OF PRODUCING SAME

(71) Applicant: Toray Industries, Inc., Tokyo (JP)

(72) Inventors: Yoji Ueda, Kamakura (JP); Emi Shimokawa, Kamakura (JP)

(73) Assignee: Toray Industries, Inc., Tokyo (JP)

(*) Notice: Subject to any disclaimer, the term of this patent is extended or adjusted under 35 U.S.C. 154(b) by 708 days.

(21) Appl. No.: 17/777,149

(22) PCT Filed: Nov. 19, 2020

(86) PCT No.: PCT/JP2020/043168
§ 371 (c)(1),
(2) Date: May 16, 2022

(87) PCT Pub. No.: WO2021/100801
PCT Pub. Date: May 27, 2021

(65) Prior Publication Data
US 2022/0396826 A1   Dec. 15, 2022

(30) Foreign Application Priority Data

Nov. 20, 2019 (JP) ................. 2019-209553

(51) Int. Cl.
*C12Q 1/6806* (2018.01)
*B01D 15/20* (2006.01)
*B01D 15/42* (2006.01)
*B01J 20/10* (2006.01)

(52) U.S. Cl.
CPC ........... *C12Q 1/6806* (2013.01); *B01D 15/20* (2013.01); *B01D 15/424* (2013.01); *B01J 20/10* (2013.01); *B01J 2220/42* (2013.01); *B01J 2220/46* (2013.01); *B01J 2220/58* (2013.01)

(58) Field of Classification Search
None
See application file for complete search history.

(56) References Cited

U.S. PATENT DOCUMENTS

| 5,234,809 | A | 8/1993 | Vikas, V et al. |
| 5,658,548 | A * | 8/1997 | Padhye ............... C12Q 1/6806 435/91.1 |
| 5,945,525 | A | 8/1999 | Uematsu et al. |
| 6,027,945 | A | 2/2000 | Smith et al. |
| 6,383,393 | B1 | 5/2002 | Colpan et al. |
| 2001/0047966 | A1 | 12/2001 | Colpan |

FOREIGN PATENT DOCUMENTS

| JP | H8-501321 A | 2/1996 |
| JP | H9-505724 A | 6/1997 |
| JP | H11-509742 A | 8/1999 |
| JP | 3329813 B2 | 9/2002 |
| JP | 2017-2232469 A | 12/2017 |
| WO | 96/18731 A2 | 6/1996 |

OTHER PUBLICATIONS

Laayoun, Ali, et al. "Aryldiazomethanes for universal labeling of nucleic acids and analysis on DNA chips." Bioconjugate chemistry 14.6 (2003): 1298-1306.*
Bert Vogelstein et al., "Preparative and analytical purification of DNA from agarose," Proc. Natl. Acad. Sci., Feb. 1979, vol. 76, No. 2, pp. 615-619 (Preview).
R. Boom et al., "Rapid and Simple Method for Purifiation of Nucleic Acids," Journal of Clinical Microbiology, Mar. 1990, vol. 28, No. 3, pp. 495-503.
Anna Heintz-Buschart et al., "Small RNA profiling of low biomass samples: identification and removal of contaminants," BMC Biology, May 14, 2018, vol. 16, Issue 1, Article No. 52, pp. 1-11.
International Search Report dated Jan. 19, 2021 in counterpart International Application No. PCT/JP2020/043168.

* cited by examiner

*Primary Examiner* — Patrick T Lewis
(74) *Attorney, Agent, or Firm* — DLA Piper LLP (US)

(57) ABSTRACT

A method reduces variation of measured data when nucleic acid is separated from a very small amount of sample followed by detection of the nucleic acid, wherein the reduction of the variation is achieved by removing contaminant nucleic acid in a nucleic acid purification column. The method of separating the nucleic acid from the sample containing the nucleic acid includes bringing the sample containing the target nucleic acid into contact with a nucleic acid-binding solid-phase carrier capable of adsorbing the nucleic acid; and eluting the nucleic acid from the nucleic acid-binding solid-phase carrier to which the nucleic acid is adsorbed.

13 Claims, 3 Drawing Sheets

8 Lines

12 Rows

NUCLEIC ACID SEPARATION METHOD, DETECTION METHOD, NUCLEIC ACID PURIFICATION COLUMN AND METHOD OF PRODUCING SAME

TECHNICAL FIELD

This disclosure relates to a method of separating a nucleic acid from a sample containing the nucleic acid, a method of detecting the separated nucleic acid, a nucleic acid purification column for separation of a nucleic acid, and a method of producing the nucleic acid purification column.

BACKGROUND

Techniques associated with separation and purification of nucleic acids such as DNA and RNA from samples such as biological samples are important in bioengineering. To obtain a reproducible, precise experimental results in detection, hybridization, amplification, sequencing and the like of a nucleic acid, it is necessary to remove impurity substances, that is, substances other than the target nucleic acid, from the sample, and to separate or isolate the nucleic acid in advance. When the sample containing the nucleic acid is a biological sample, examples of the impurity substances include proteins, carbohydrates, lipids, and polyphenols.

A variety of approaches have been carried out in separation of nucleic acids from biological samples. Examples of such approaches include extraction methods using an organic solvent such as ethanol precipitation; purification of nucleic acid using dialysis or an ultrafiltration membrane; and separation using a nucleic acid-binding solid-phase carrier.

Among them, ethanol precipitation is a widely used method, and the method enables separation of nucleic acid by a simple operation. However, the method has problems in that the recovery of the nucleic acid is generally low, and that the recovery varies depending on the operation method. Purification methods using dialysis or an ultrafiltration membrane are also employed, but they have a limitation regarding the molecular weight, and moreover, the samples to which the methods are applicable are limited.

Concerning methods of separation using a nucleic acid-binding solid-phase carrier, examples of the methods commonly used in recent years include a method in which a target nucleic acid in a sample is bound to a solid-phase carrier in the presence of a chaotropic agent to separate the nucleic acid (U.S. Pat. No. 6,027,945 B and R. Boom et al., 1990, J Clin Microbiol., 28(3): 495-503). That method is called the Boom method. It is a nucleic acid purification method based on the utilization of the following properties of nucleic acid: nucleic acid binds to a solid-phase carrier such as silica in the presence of a chaotropic agent such as guanidinium salt or urea; and nucleic acid bound to a solid-phase carrier can be eluted by water. In the procedure of the nucleic acid purification using the Boom method, a solution containing nucleic acid is brought into contact with a solid-phase carrier such as silica in the presence of a chaotropic agent to allow adsorption of the nucleic acid in the sample to the solid-phase carrier, and then a washing liquid is passed through the carrier to wash away unnecessary components such as salts, followed by elution of the nucleic acid using water or the like.

In separation of a target nucleic acid from a biological sample using an existing method such as the method described above, when the biological sample is available only in a very small amount, the amount of the nucleic acid obtained by the separation is also very small. Therefore, for analysis or detection of the very small amount of nucleic acid thus separated, a highly sensitive analysis method needs to be employed. For example, when quantification using UV absorbance or fluorescence is technically difficult such as when the amount is under the detection limit (for example, when the amount of nucleic acid is less than 1 ng), a nucleic acid amplification technique by polymerase chain reaction (PCR) or the like is applied, and then sequencing, electrophoretic detection, highly sensitive detection using a nucleic acid microarray or the like is carried out. The LC/MS/MS method, which directly analyzes nucleic acid molecules by mass spectrometry (JP 2017-223469 A) and the like are also employed.

A. Heintz-Buschart et al., 2018, BMC Biology, 16:52 reports that, when analysis was carried out for RNA obtained by purification from a human sample using a commercially available nucleic acid purification column, nucleic acid not derived from the human sample was detected. A. Heintz-Buschart et al. revealed that the nucleic acid purification column product was contaminated with the nucleic acid, and reported that the attempt to remove the nucleic acid failed when washing with water alone was carried out.

When a very small amount of target nucleic acid is to be detected as described above when the nucleic acid purification column used for the purification of the nucleic acid is contaminated with a nucleic acid impurity, variation of the measured data of the target nucleic acid increases, which is problematic. In particular, when a nucleic acid amplification technique is applied, or a highly sensitive nucleic acid microarray is used as described above, it is extremely important to reduce variation of data among experiments from the viewpoint of achieving reliable nucleic acid analysis. It could therefore be helpful to provide a method of reducing variation of measured data when a very small amount of sample such as a nucleic acid in an amount of, for example, about 1 ng is separated for detection of the nucleic acid, wherein the reduction of the variation is achieved by removing contaminant nucleic acid in a nucleic acid purification column.

SUMMARY

We discovered that, when a target nucleic acid is separated (purified) from a sample containing the nucleic acid using a nucleic acid purification column containing a nucleic acid-binding solid-phase carrier, variation in measurement of the separated target nucleic acid can be reduced by preliminarily bringing the nucleic acid-binding solid-phase carrier into contact with a solution containing a chaotropic agent to remove contaminant nucleic acid in the nucleic acid purification column.

We thus provide:

[1] A method of separating a nucleic acid from a sample containing the nucleic acid, the method comprising (1) and (2):

(1) bringing the sample containing the target nucleic acid into contact with a nucleic acid-binding solid-phase carrier capable of adsorbing the nucleic acid; and (2) eluting the nucleic acid from the nucleic acid-binding solid-phase carrier to which the nucleic acid is adsorbed in (1);

wherein the nucleic acid-binding solid-phase carrier is brought into contact with a solution containing a chaotropic agent before (1).

[2] The method according to [1], further comprising a step of washing the nucleic acid-binding solid-phase carrier with water or an aqueous alcohol solution after bringing the nucleic acid-binding solid-phase carrier into contact with the solution containing the chaotropic agent.

[3] The method according to [1] or [2], wherein the nucleic acid-binding solid-phase carrier is a silica membrane.

[4] The method according to any one of [1] to [3], wherein the chaotropic agent is any of guanidinium salt, urea, iodide salt, chloric acid salt, perchloric acid salt, thiocyanic acid salt, and isothiocyanic acid salt.

[5] The method according to any one of [1] to [4], wherein the solution containing the chaotropic agent contains an alcohol.

[6] The method according to [5], wherein the alcohol is ethanol.

[7] The method according to any one of [1] to [6], wherein the nucleic acid is DNA or RNA.

[8] A method of detecting a nucleic acid, the method comprising (1), (2), and (3):
   (1) bringing a sample containing the target nucleic acid into contact with a nucleic acid-binding solid-phase carrier capable of adsorbing the nucleic acid;
   (2) eluting the nucleic acid from the nucleic acid-binding solid-phase carrier to which the nucleic acid is adsorbed in (1); and
   (3) labeling and detecting the eluted nucleic acid;
   wherein the nucleic acid-binding solid-phase carrier is brought into contact with a solution containing a chaotropic agent before (1).

[9] A nucleic acid purification column comprising: a hollow body in which an inlet opening section and an outlet opening section are formed; and a nucleic acid-binding solid-phase carrier;
   which nucleic acid purification column is produced by a method comprising allowing a solution containing a chaotropic agent to flow through the nucleic acid-binding solid-phase carrier, and then drying the nucleic acid-binding solid-phase carrier.

[10] A method of producing a nucleic acid purification column, the column comprising: a hollow body in which an inlet opening section and an outlet opening section are formed; and a nucleic acid-binding solid-phase carrier;
   the method comprising allowing a solution containing a chaotropic agent to flow through the nucleic acid-binding solid-phase carrier, and then drying the nucleic acid-binding solid-phase carrier.

[11] The method according to [10], further comprising a step of washing the nucleic acid-binding solid-phase carrier with water or an aqueous alcohol solution after allowing the solution containing the chaotropic agent to flow through the nucleic acid-binding solid-phase carrier.

[12] The method according to [10] or [11], wherein allowing the solution to flow is carried out in a state where the nucleic acid-binding solid-phase carrier is packed in the hollow body.

[13] The method according to any one of [10] to [12], wherein the nucleic acid-binding solid-phase carrier is a silica membrane.

[14] The method according to any one of [10] to [13], wherein the chaotropic agent is guanidinium salt, urea, iodide salt, chloric acid salt, perchloric acid salt, thiocyanic acid salt, or isothiocyanic acid salt.

We thus enable reduction of variation in measurement of a target nucleic acid separated/purified from a sample containing the nucleic acid.

DESCRIPTION OF SYMBOLS

Figure 1:
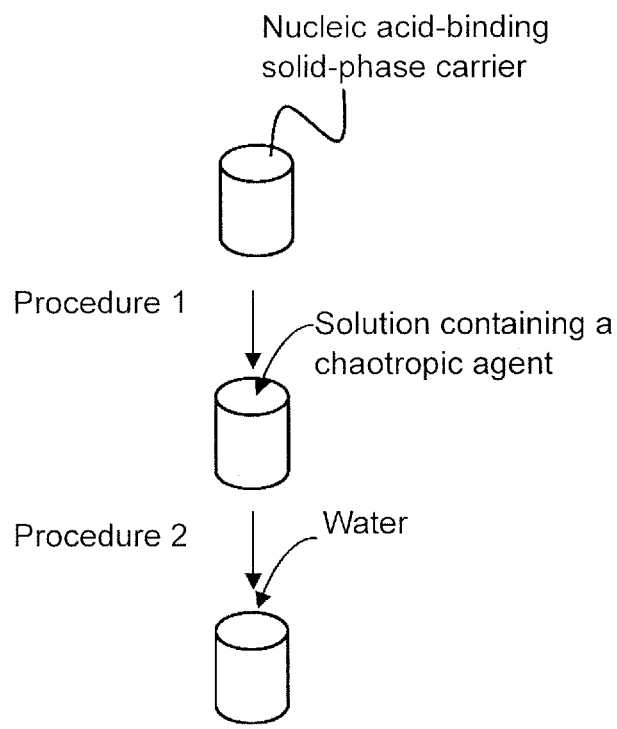
FIG. 1 is a diagram showing the process of the treatment of the nucleic acid-binding solid-phase carrier by the solution containing the chaotropic agent in our method.

1. Hollow body
2. Inlet opening section
3. Rim
4. Fixing member
5. Nucleic acid-binding solid-phase carrier
6. Outlet opening section
7. Support
8. Container

DETAILED DESCRIPTION

The sample to be subjected to the nucleic acid purification column is not limited as long as the sample potentially contains a nucleic acid. Examples of the sample include samples potentially containing a certain nucleic acid such as samples derived from animals, samples derived from plants, and samples derived from microorganisms including fungi and bacteria. Examples of the samples derived from animals include, but are not limited to, body fluid samples such as blood, serum, plasma, urine, stool, spinal fluid, saliva, swab, and various tissue fluids; various tissues; and formalin-fixed paraffin-embedded samples (FFPE).

The target nucleic acid is not limited. For example, DNA or RNA contained in the sample may be used. Nucleic acids obtained by in vitro chemical reaction or enzymatic reaction treatment of these nucleic acids may also be used. Examples of the DNA include chromosomal DNA, viral DNA, bacterial or fungal DNA, cDNA obtained by reverse transcription of RNA, and partial fragments thereof. When the nucleic acid is a DNA, it may be either double-stranded DNA or single-stranded DNA. Examples of the RNA include messenger RNA, ribosomal RNA, small RNA, microRNA, and partial fragments thereof. Nucleic acids such as chemically synthesized DNA or RNA may also be used as the target nucleic acid.

The nucleic acid-binding solid-phase carrier (—"solid-phase carrier" or "carrier") is not limited as long as it is capable of adsorbing a nucleic acid. The "nucleic acid-binding" means a substance capable of forming a hydrophobic bond with a nucleic acid in the coexistence of a chaotropic salt.

Preferred examples of the material of the solid-phase carrier include: inorganic materials such as silica, glass, alumina, zeolite, and clay minerals; and polymer materials such as polystyrene. Specific examples of the material include silica-based materials such as the material described in U.S. Pat. No. 5,234,809 B; and polymer materials including latex and polystyrene-based materials such as the material described in WO 96/18731. Examples of the shape of the solid-phase carrier include particles, beads, sheets (films and membranes), woven fabrics, and fibers. The solid-phase carrier is especially preferably a silica membrane. A silica membrane is a film-shaped product composed of silica, glass, or quartz fibers, or is a thin film composed of silica gel. It is disclosed in JP 3329813 B or JP 8-501321 A.

In the use of each of these solid-phase carriers, the carrier may be packed into a column, and a sample solution or the like may be passed therethrough. Alternatively, the carrier may be immersed as it is in a sample solution or the like, to be used in the suspended state.

When the solid-phase carrier is used in the suspended state, magnetic particles are also preferably used as the solid-phase carrier since they can be simply separated from the suspension by using a magnetic field. Examples of common materials used for the magnetic particles include magnetic metal oxides, especially iron oxides. Examples of the useful magnetic oxides include iron oxides whose ferrous iron is arbitrarily entirely or partially substituted by a divalent transition metal(s) such as calcium, chromium, cobalt, copper, magnesium, manganese, nickel, vanadium, and/or zinc. Examples of the silica-based magnetic particles include the particles described in U.S. Pat. Nos. 6,027,945 B and 5,945,525 B.

In general, a nucleic acid purification column is a column packed with a solid-phase carrier, and used to separate nucleic acid in a sample solution by passing the solution through the column.

Nucleic acid purification columns using a silica membrane as the solid-phase carrier are commercially available from a plurality of manufacturers. Representative examples of such columns include nucleic acid purification columns contained in nucleic acid purification kits such as "miRNeasy serum/plasma kit" (model number, 217184), "miRNeasy 96 kit" (model number, 217061, *), "miRNeasy Mini Kit" (model number, 217004), "QIAamp DNA mini kit" (model number, 51304), "RNeasy micro kit" (model number, 74004), "RNeasy UCP micro kit" (model number, 73934), and "RNeasy MinElute Cleanup Kit" (model number, 74204), manufactured by QIAGEN; "NucleoSpin miRNA Plasma" (model number, 740981.1), "NucleoSpin RNA" (model number, 740955.1), "NucleoSpin 96 RNA" (model number, 740709.24, *), "NucleoSpin 8 RNA" (model number, 740698), and "NucleoSpin RNA Plus" (model number, 740984.1), manufactured by MACHEREY-NAGEL; "RNA Clean & Concentrator Kit" (model number, R1080, *), "RNA Clean & Concentrator-5" (model number, R1013), "RNA Clean & Concentrator-25" (model number, R1017), "UNIFILTER Microplate, 96-well, 800 μl, DNA binding, clear polystyrene" (model number, 7700-2810, *), and "UNIFILTER Microplate, 96-well, 800 μl, GF/C, clear polystyrene, filter bottom with long drip director" (model number, 7700-2801*), manufactured by Zymo Research; and "mirVana miRNA Isolation Kit, with phenol" (model number, AM1560), "PureLink miRNA Isolation Kit" (model number, K157001), and "PureLink RNA Mini Kit" (model number, 12183018A), manufactured by Thermo Fisher. The method of separating a nucleic acid is applicable when the target nucleic acid is separated using these commercially available nucleic acid purification columns. Kits containing nucleic acid purification columns of the later-mentioned 96-well plate format are marked with an asterisk after the model number.

Nucleic acid purification columns using the magnetic particles as a solid-phase carrier are commercially available from a plurality of manufacturers. Representative examples of such columns include nucleic acid purification columns contained in nucleic acid purification kits such as "Maxwell RSC miRNA from Tissue and Plasma or Serum" (model number, AS1680) and "Maxwell RSC Whole Blood DNA Kit" (model number, AS1520), manufactured by Promega; "RNAdvance Blood Kit" (model number, A35604) and "RNAdvance Cell v2 Kit" (model number, A47942), manufactured by Beckman; and "MagMAX mirVana Total RNA Isolation Kit" (model number, A27827) and "Dynameads mRNA Purification Kit" (model number, 61006), manufactured by Thermo Fisher.

A first step in our method of separating a nucleic acid is a step of bringing a sample containing a target nucleic acid into contact with a solid-phase carrier to allow adsorption of the nucleic acid in the sample to the solid-phase carrier. When the solid-phase carrier is used in the state where it is packed in a column, the step may be carried out by passing a sample solution through the column, and, when necessary, removing the sample solution in the column by separation using centrifugation or suction. More specifically, the sample solution containing the target nucleic acid is placed on the column packed with the solid-phase carrier. The sample solution can pass through the solid-phase carrier under the own weight, but, when it takes a long time, the column on which the sample solution is placed may be centrifuged to pass the sample solution through the solid-phase carrier. The centrifugation conditions are appropriately set depending on the shape of the column. In a column packed with a commercially available solid-phase carrier, the centrifugation may be carried out at 8000×g to 10,000×g.

Alternatively, instead of packing the solid-phase carrier into the column, the solid-phase carrier may be immersed as it is in a sample solution, and then the solution may be removed by separation using centrifugation, suction or the like. More specifically, an arbitrary amount of a solid-phase carrier is added to a sample containing a nucleic acid to immerse the carrier in the sample. In this method, a solid-phase carrier in the form of particles or beads is preferably used. After the immersion, the solid-phase carrier to which the nucleic acid is bound may be recovered by precipitating the solid-phase carrier to the bottom of the solution by centrifugation, and then removing the supernatant. The centrifugation conditions in this process may be appropriately set based on the specific gravity of the solid-phase carrier. When the specific gravity of the solid-phase carrier is sufficiently high, the solid-phase carrier precipitates to the bottom even without centrifugation so that the solid-phase carrier can be recovered by removing the supernatant.

A second step in our method of separating a nucleic acid is a step of eluting the nucleic acid that has adsorbed to the solid-phase carrier in the first step, from the solid-phase carrier. The elution of the nucleic acid may be carried out using water or a low-polarity solvent such as TE buffer as an eluent. When the solid-phase carrier is used in the state where it is packed in a column, the eluent may be passed through the column, and, when necessary, the eluent in the column may be separated by centrifugation or suction to obtain an eluate containing the nucleic acid. When the solid-phase carrier is used without being packed in a column, the solid-phase carrier may be immersed as it is in an eluent, and then the solid-phase carrier may be removed by separation using centrifugation, suction or the like to obtain an eluate containing eluted nucleic acid.

Since the first and second steps per se are well known, they may be carried out by conventional methods.

The method of separating a nucleic acid is characterized in that, before carrying out the first step of bringing the sample containing the target nucleic acid into contact with the solid-phase carrier to allow adsorption of the nucleic acid in the sample to the solid-phase carrier, the solid-phase carrier is brought into contact with a solution containing a chaotropic agent.

A chaotropic agent generally means a substance that reduces the interaction between water molecules to destabilize the structure of nucleic acid in a solution. Nucleic acid has secondary structures due to hydrogen bonds between bases. By adding a chaotropic agent, the secondary structures are dissociated.

Examples of the chaotropic agent include guanidinium salt, urea, iodide salt, chloric acid salt, perchloric acid salt, thiocyanic acid salt, and isothiocyanic acid salt. Preferred examples of the chaotropic agent include guanidinium thiocyanate and guanidinium hydrochloride. The concentration of the solution containing the chaotropic agent is preferably 1 M to 8 M.

The solution containing the chaotropic agent may be used as an aqueous solution. The aqueous solution may be an aqueous solution containing alcohol. The alcohol is preferably ethanol, which is commonly used in molecular biological experiments. The concentration of the alcohol in the solution containing the chaotropic agent may be 10 to 80% by volume.

Regarding the method of bringing the solid-phase carrier into contact with the solution containing the chaotropic agent, when the solid-phase carrier is used in the state where it is packed in a column, the solution containing the chaotropic agent may be passed (allowed to flow) through the column, and, when necessary, the solution in the column may be separated by centrifugation or suction. When the solid-phase carrier is used without being packed in a column, the solid-phase carrier may be immersed as it is in the solution containing the chaotropic agent, and then the solution may be removed by separation using centrifugation, suction, or the like. In this process, the amount of the solution containing the chaotropic agent used is about 0.1 mL to 1.5 mL, preferably about 0.6 mL to 1.0 mL, per 10 mg of the solid-phase carrier. The temperature for carrying out the method is not limited, and is usually about 4° C. to 60° C. The method is preferably carried out at room temperature from the viewpoint of simplicity. After the solid-phase carrier is brought into contact with the chaotropic agent, the solid-phase carrier is preferably washed with water or an aqueous alcohol solution such as 10 to 80% by volume ethanol. The amount of the water or aqueous alcohol solution used in this process is not limited, and is usually about 0.1 mL to 1.5 mL per 10 mg of the solid-phase carrier.

One example of the step of bringing the solution containing the chaotropic agent into contact with the solid-phase carrier is schematically shown in FIG. 1. First, the solution containing the chaotropic agent is passed through the solid-phase carrier, and then the solution is removed by a method such as centrifugation or suction (Procedure 1). Subsequently, when necessary, water is passed through the solid-phase carrier, and then removed by a method such as centrifugation or suction (Procedure 2). An aqueous alcohol solution such as 10 to 80% by volume ethanol may be used instead of the water. The thus provided solid-phase carrier may be used for the separation of the sample containing the nucleic acid.

The method of detecting a nucleic acid comprises a third step of detecting the target nucleic acid, which is carried out after bringing the solid-phase carrier into contact with the solution containing the chaotropic agent as described above, and obtaining the target nucleic acid by carrying out the first and second steps.

The detection of the nucleic acid may be carried out by labeling with a labeling substance. When the nucleic acid is a DNA, for the labeling of the nucleic acid, an enzyme such as DNA polymerase or terminal deoxitidil transferase may be used to incorporate the labeling substance. When the nucleic acid is detected by electrophoresis, the labeling may be carried out by incorporating an intercalator such as ethidium bromide.

When the nucleic acid is an RNA, a method in which a labeling substance is bound to the 3'-end of the RNA, a method in which a labeling substance is bound to the 5'-end of the RNA, or a method in which a labeling substance is bound to a nucleoside(s) may be used, or a combination of these methods may be used. In the method in which a labeling substance is bound to the 3'-end, and the method in which a labeling substance is bound to the 5'-end, enzymatic reaction may be used. For the enzymatic reaction, T4 RNA ligase, terminal deoxitidil transferase, poly (A) polymerase or the like may be used. For any of these labeling methods, one may refer to, for example, a method described in "miRNA Experimental Protocols" (Yodosha Co., Ltd., 2008). The above-described DNA labeling methods may also be used after replacing the RNA by the DNA complementary strand using reverse transcriptase.

The labeling substance may be a nucleic acid containing one or more labeling bodies. The labeling substance may contain a linker sequence that is a polymer of at least two or more nucleic acids.

Examples of the labeling bodies that may be used include known substances to be used for labeling such as fluorescent dyes, phosphorescent dyes, and radioisotopes. The labeling body is preferably a fluorescent dye since it allows simple measurement and easy detection of the signal. Specific examples of the fluorescent dye include known fluorescent dyes such as Cyanine (Cyanine 2), aminomethylcoumarin, fluorescein, indocarbocyanine (Cyanine 3), Cyanine 3.5, tetramethylrhodamine, rhodamine red, Texas red, indocarbocyanine (Cyanine 5), Cyanine 5.5, Cyanine 7, and Oyster.

For the detection of the fluorescent dye, a fluorescence microscope, fluorescence scanner or the like may be used.

When the nucleic acid is a DNA, examples of the method of detecting the nucleic acid include PCR, sequencing, and hybridization. When the nucleic acid is an RNA, it can be detected by PCR, sequencing, hybridization, or the like after converting the RNA to a DNA fragment(s) by reverse transcriptase. Further, when the nucleic acid is an RNA, the RNA may be hydrolyzed into monomers, and may then be detected by LC/MS/MS.

The above third step is well known, and may be carried out by a conventional method.

Variation of the measured data may be expressed using the coefficient of variation as an index. The coefficient of variation is obtained by dividing the standard deviation of values obtained by a plurality of times of measurement, by the mean, and then multiplying the resulting value by 100. The lower the coefficient of variation, the smaller the variation of the measured data. In general, the variation of measured data can be said to be small when the coefficient of variation is less than 5%.

The nucleic acid purification column comprises: a hollow body (tube) in which an inlet opening section and an outlet opening section are formed; and a nucleic acid-binding solid-phase carrier; which nucleic acid purification column is produced by a method comprising a "step of allowing a solution containing a chaotropic agent to flow through the nucleic acid-binding solid-phase carrier, and then drying the nucleic acid-binding solid-phase carrier."

Figure 2:
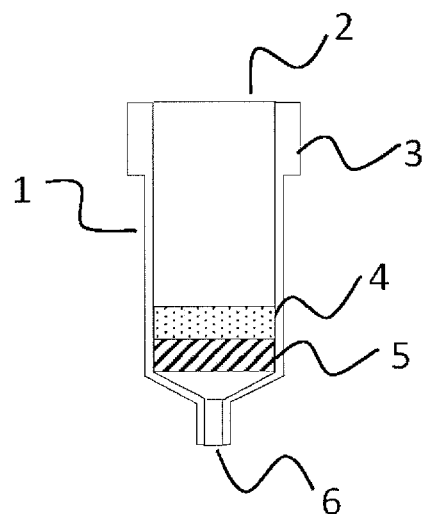
FIG. 2 is a cross-sectional view showing one example of our nucleic acid purification column.

FIG. 2 shows one example of our nucleic acid purification column. A hollow body 1 has a structure having a cylindrical shape, wherein an inlet opening section 2 for injection of a sample solution and an outlet opening section 6 for discharging the solution that has passed through a solid-phase carrier 5 are formed. Examples of materials of the hollow body 1 that may be used include the same materials as those of existing nucleic acid purification columns, for example, resins such as polypropylene, polyethylene, polymethyl methacrylate, polytetrafluoroethylene, polyethyl terephthalate, and polyacrylonitrile; and glasses.

The inside of the hollow body 1 is packed with the nucleic acid-binding solid-phase carrier 5. A fixing member 4 for fixing the solid-phase carrier 5 may be mounted in the inlet-opening-section side. The same resin materials as those for the hollow body 1 may be used for the fixing member 4. Preferably, the fixing member 4 has an outer diameter that is the same as the inner diameter of the hollow body 1, and has an O-ring structure in which the center portion is cut away.

Figure 4:
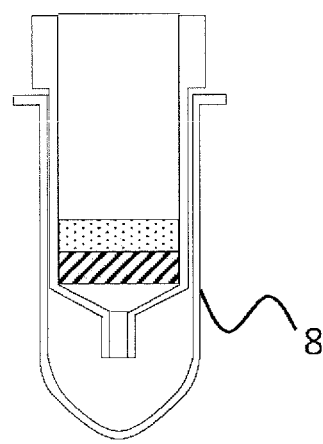
FIG. 4 is a cross-sectional view showing combination of our nucleic acid purification column with a container.

The hollow body 1 may comprise a rim 3. By providing the rim 3, when the present device is used together with a centrifuge, the device can be attached to a container 8 as illustrated in FIG. 4.

Figure 3:
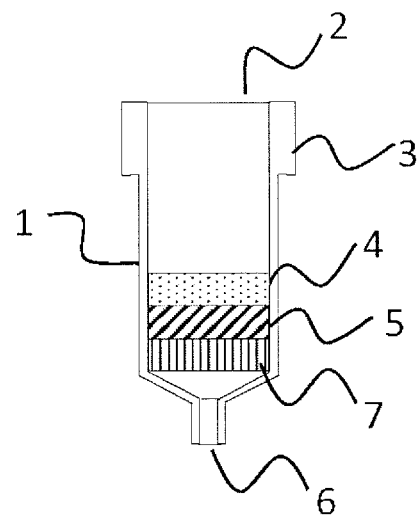
FIG. 3 is a cross-sectional view showing another example of our nucleic acid purification column.

FIG. 3 illustrates another example of our nucleic acid purification column. A support 7 for retaining the solid-phase carrier 5 may be provided, for example, to prevent deformation or falling-off of the solid-phase carrier 5 during the centrifugation. The support 7 may have a microporous structure having a size which does not allow passing of the solid-phase carrier 5, but which allows passing of a solution. A membrane made of sintered glass, polypropylene, glass, ceramic, or a plastic such as nylon; or a non-woven fabric made of polypropylene, polyethylene, nylon or the like may be used therefor.

Figure 5:
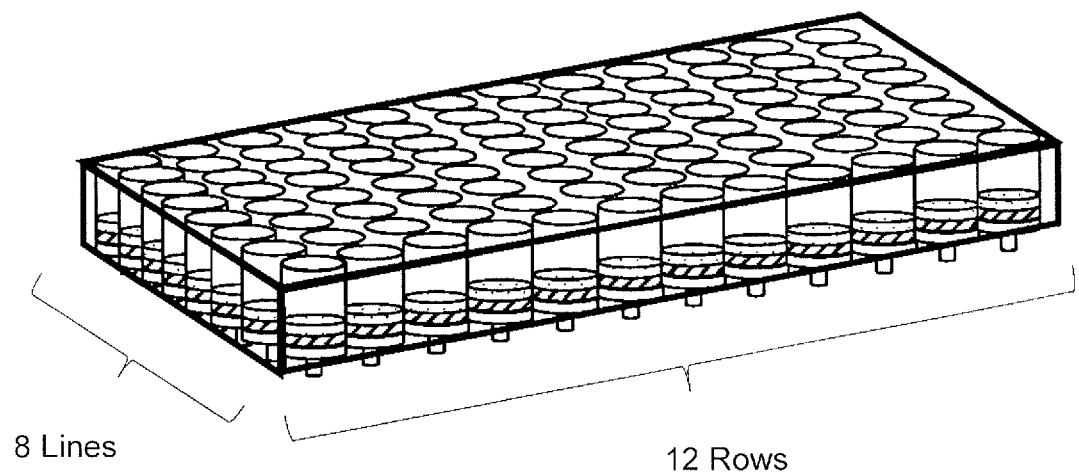
FIG. 5 is a perspective view showing another example of our nucleic acid purification column.

FIG. 5 shows a 96-well plate format as another example of our nucleic acid purification column. The format has a structure in which 8×12 units of the nucleic acid purification column shown in FIG. 2 or 3 are arranged, which units are bound to each other at the circumference of the hollow body 1. In each unit, an inlet opening section 2, and an outlet opening section 6 for discharging the solution that has passed through the solid-phase carrier 5 are formed. The solution may be discharged by separation removal using centrifugation or suction. Columns having a 96-well-plate format are commercially available as products in the form of a plate in which a plurality of columns are combined. However, the number of columns and their arrangement are not limited to 8×12. Other numbers of columns and other arrangements (different numbers of lines and numbers of rows) may also be employed.

The nucleic acid purification column comprising: a hollow body in which an inlet opening section and an outlet opening section are formed; and a nucleic acid-binding solid-phase carrier; may be produced by the following procedures.

First, the solid-phase carrier 5 is packed into the hollow body 1. In this process, when the solid-phase carrier 5 is in the form of particles or beads, their packing may be carried out as they are using a dispensing spoon or the like, or may be carried out by dispersing the particles or beads in a solvent such as water or a buffer, and pouring the resulting suspension using a pipette or the like. When the solid-phase carrier 5 is in the form of a sheet or woven fabric, the solid-phase carrier 5 may be cut to the same size as the inner diameter of the hollow body 1, and may then be packed into the hollow body 1, followed by, when necessary, fitting the fixing member 4 having an O-ring structure on the solid-phase carrier 5 to fix the solid-phase carrier 5.

The nucleic acid purification column is produced by a method comprising the step of allowing a solution containing a chaotropic agent to pass (to flow) through a nucleic acid-binding solid-phase carrier, and then drying the nucleic acid-binding solid-phase carrier.

The solution containing the chaotropic agent may be the same as the solution used in the method of separating the nucleic acid. Specific examples of solutions that may be preferably used include aqueous solutions and alcohol-containing aqueous solutions containing guanidinium salt, urea, iodide salt, chloric acid salt, perchloric acid salt, thiocyanic acid salt, and isothiocyanic acid salt or the like as a chaotropic agent at a concentration of 1 M to 8 M.

Similarly to the method of separating the nucleic acid shown in FIG. 1, the method of allowing the solution containing the chaotropic agent to pass (to flow) through the nucleic acid-binding solid-phase carrier may be carried out by allowing the solution containing the chaotropic agent to pass (to flow) through the column in the state where the column is packed with the solid-phase carrier, and then separating the solution by centrifugation or suction (Procedure 1), followed by, when necessary, passing water or an aqueous alcohol solution such as 10 to 80% by volume ethanol through the column and removing it by centrifugation or suction (Procedure 2).

Alternatively, the step of passing the solution containing the chaotropic agent through the nucleic acid-binding solid-phase carrier may be carried out before packing the column with the solid-phase carrier. More specifically, the step may be carried out by immersing the solid-phase carrier in the solution containing the chaotropic agent, and then, when necessary, immersing the solid-phase carrier in water, followed by separation removal of the solution using centrifugation or suction.

After the solution containing the chaotropic agent is allowed to pass (to flow) through the nucleic acid-binding solid-phase carrier, the carrier is preferably washed with water or an aqueous alcohol solution as described above, followed by drying the nucleic acid-binding solid-phase carrier. When the solid-phase carrier is in the state where it is packed in a hollow body, the drying may be carried out by air drying. More specifically, the solid-phase carrier may be left to stand for several minutes to not less than several hours to evaporate water in the solid-phase carrier. Alternatively, the solid-phase carrier may be left to stand in a heated oven to evaporate water in the solid-phase carrier. The temperature in this example may be appropriately set depending on, for example, the materials of the hollow body, the fixing member, and the support. The heating is preferably carried out at 20° C. to 80° C. Also, when the solution containing the chaotropic agent is passed through the solid-phase carrier before packing the solid-phase carrier into the column, the solid-phase carrier may be dried in the same manner, and may then be packed into the hollow body. In such instances, as described above, when necessary, the solid-phase carrier may be fixed by fitting a fixing member having an O-ring structure on the solid-phase carrier to prepare the nucleic acid purification column.

As described above, nucleic acid purification columns comprising a solid-phase carrier are commercially available. Therefore, as described in the Examples below, production of the nucleic acid purification column is possible also by passing a chaotropic agent through a commercially available nucleic acid purification column as described above, and then, preferably, washing the solid-phase carrier with water or an aqueous alcohol solution, followed by drying the solid-phase carrier.

EXAMPLES

Our columns and methods are described in detail by way of the following Examples. However, the technical scope of this disclosure is not limited by the Examples.

In the following Examples and the Comparative Examples, the following commercially available nucleic acid purification columns comprising a nucleic acid-binding solid-phase carrier were used (Table 1):

- the nucleic acid purification column contained in the nucleic acid purification kit "miRNeasy Mini Kit," manufactured by QIAGEN ("Column A"), which column uses a silica membrane having a diameter of 8 mm;
- the nucleic acid purification column contained in the nucleic acid purification kit "NucleoSpin miRNA Plasma," manufactured by MACHEREY-NAGEL ("Column B"), which column uses a silica membrane having a diameter of 8 mm;
- the nucleic acid purification column contained in the nucleic acid purification kit "RNeasy 96 kit," manufactured by QIAGEN ("Column C");
- the nucleic acid purification column contained in the nucleic acid purification kit "RNeasy UCP micro kit," manufactured by QIAGEN ("Column D");
- the nucleic acid purification column contained in the nucleic acid purification kit "RNA Clean & Concentrator Kit," manufactured by Zymo Research ("Column E"); and
- the nucleic acid purification column contained in the nucleic acid purification kit "96 Well 800 µl UNIFILTER Microplate," manufactured by cytiva ("Column F").

Further, an untreated column was provided by omitting the step of passing the solution containing the chaotropic agent through the solid-phase carrier (Comparative Example 1).

(2) Preparation of Sample Containing Nucleic Acid, and Separation of Nucleic Acid Using "Isogen LS" (Nippon Gene Co., Ltd.), a solution containing nucleic acid was obtained from 300 µL of human serum, and the nucleic acid was separated using the above-described Column A or Column B. To verify the reproducibility, the separation was carried out four times with Column A, and three times with Column B, to obtain samples to be individually subjected to detection of nucleic acid.

First, to the above-described solution containing nucleic acid obtained from 300 µL of human serum, 1.5 volumes of ethanol was added, and the resulting mixture was placed on Column A or Column B. By centrifuging the column at 12,000×g for 1 minute, the solution containing nucleic acid was brought into contact with the solid-phase carrier in the column to allow adsorption of the nucleic acid contained in the solution to the solid-phase carrier. Subsequently, the washing liquid included in the nucleic acid purification kit including Column A or Column B, respectively, was placed on the column, and centrifuged at 12,000×g for 1 minute to wash away components other than the nucleic acid remaining in the column. Finally, 70 µL of water was placed on the column, and then the column was centrifuged at 12,000×g for 1 minute to obtain an eluate containing the nucleic acid.

TABLE 1

| Nucleic acid purification column | Commercially available nucleic acid purification kit product name | Column manufacturer | Model number | Shape of purification column |
|---|---|---|---|---|
| A | miRNeasy Mini Kit | Qiagen | 217004 | Spin column |
| B | NucleoSpin miRNA Plasma | MACHEREY-NAGEL | 740981.1 | Spin column |
| C | RNeasy 96 kit | Qiagen | 74181 | 96-Well plate format |
| D | RNeasy UCP micro kit | Qiagen | 73934 | Spin column |
| E | RNA Clean & Concentrator Kit | Zymo Research | R1080 | 96-Well plate format |
| F | 96 Well 800 µl UNIFILTER Microplate | cytiva | 7700-2810 | 96-Well plate format |

Examples 1 and 2, and Comparative Examples 1 and 2

(1) Step of Passing Solution Containing Chaotropic Agent Through Nucleic Acid-Binding Solid-Phase Carrier As a nucleic acid-binding solid-phase carrier, Column A or Column B was used.

The step of passing the solution containing the chaotropic agent through the nucleic acid-binding solid-phase carrier of the nucleic acid purification column was carried out by the following procedures. First, 800 µL of the solution containing the chaotropic agent was placed on the column, and then the column was centrifuged at 12,000×g for 1 minute to remove the solution. In this step, as the solution containing the chaotropic agent, 1.3 M guanidine hydrochloride solution (Example 1) or a solution of 1.3 M guanidine hydrochloride in 67% ethanol (Example 2) was used. Subsequently, 800 µL of water was placed on the column, and then the column was centrifuged at 12,000×g for 1 minute to remove the water.

For comparison of the effect, a column was provided in the same manner as described above except that 67% ethanol was passed through the column instead of the solution containing the chaotropic agent (Comparative Example 2).

(3) Measurement of Nucleic Acid by DNA Microarray

Using a "3D-Gene' human miRNA oligo chip" manufactured by Toray Industries, Inc. (compatible with miRBase release 21; capable of detection of 2556 kinds of miRNAs), the following experiment was carried out.

Nucleic acid in the eluate obtained as described above was labeled using a "3D-Gene' miRNA labeling kit" (manufactured by Toray Industries, Inc.). The labeled nucleic acid (RNA) was subjected to hybridization and washing according to the standard protocol for the "3D-Gene' miRNA chip" (manufactured by Toray Industries, Inc.). The fluorescence signal from the reacted DNA microarray was detected using a "Microarray Scanner" (manufactured by Toray Industries, Inc.), and the number of miRNAs for which a signal significantly higher than the background noise was obtained was determined. For this value, the standard deviation and the coefficient of variation among the plurality of times of measurement were determined (Table 1).

As a result, when Column A was used, 1535 miRNAs on average were detected in Comparative Example 1 (no treatment). The standard deviation was 130, indicating a large variation among the plurality of times of measurement. In Comparative Example 2 (in which 67% ethanol was allowed to flow), the number of detected miRNAs varied similarly to Comparative Example 1. The coefficient of variation was 8.5% in Comparative Example 1, and 6.6% in Comparative Example 2.

On the other hand, in Example 1 (in which 1.3 M guanidine hydrochloride solution was allowed to flow), the average number of detected miRNAs was 1451; the standard deviation was 34; and the coefficient of variation was 2.4%. In Example 2 (in which the solution of 1.3 M guanidine hydrochloride in 67% ethanol was allowed to flow), the average number of detected miRNAs was 1407; the standard deviation was 21; and the coefficient of variation was 1.5%. Thus, both Example 1 and 2 showed a variation much smaller than those in Comparative Examples 1 and 2.

When Column B was used, 1593 miRNAs on average were detected in Comparative Example 1 (no treatment). The standard deviation was 82, indicating a large variation among the plurality of times of measurement. In Comparative Example 2, the number of detected miRNAs varied similarly to Comparative Example 1. The coefficient of variation was 5.1% in Comparative Example 1, and 5.6% in Comparative Example 2.

On the other hand, in Example 1 (in which 1.3 M guanidine hydrochloride solution was allowed to flow), the average number of detected miRNAs was 1548; the standard deviation was 47; and the coefficient of variation was 3.0%. In Example 2 (in which the solution of 1.3 M guanidine hydrochloride in 67% ethanol was allowed to flow), the average number of detected miRNAs was 1401; the standard deviation was 18; and the coefficient of variation was 1.3%. Thus, both Examples 1 and 2 showed a variation much smaller than those in Comparative Examples 1 and 2.

Since Columns C, E, and F have a 96-well-plate format, their centrifugal acceleration condition for the removal of the solution was set to 3000×g.

For comparison, a column was provided in the same manner except that sterile purified water was used instead of the solution containing the chaotropic agent (Comparative Example 3).

In the same manner as in Examples 1 and 2, separation of nucleic acid from the prepared nucleic acid sample was carried out using each column, and then measurement of the nucleic acid was carried out using the DNA microarray. From the measured values, the standard deviation and the coefficient of variation of the number of detected miRNAs among the plurality of times of measurement were determined (Table 3).

As a result of the analysis, the coefficient of variation under the condition where sterile purified water was allowed to flow in Comparative Example 3 was found to be 5.2% to 5.9%. On the other hand, the coefficient of variation under the condition where the chaotropic agent was allowed to flow in Example 3 was found to be 1.2% to 1.9%. Thus, all columns to which our method was applied showed a variation-reducing effect.

TABLE 2

| Chaotropic agent that was allowed to flow | | Example 1 1.3M Aqueous guanidine hydrochloride solution | Example 2 Solution of 1.3M guanidine hydrochloride in 67% ethanol | Comparative Example 1 No treatment | Comparative Example 2 67% Ethanol |
|---|---|---|---|---|---|
| Column A | 1st | 1458 | 1407 | 1484 | 1458 |
|  | 2nd | 1460 | 1432 | 1535 | 1509 |
|  | 3rd | 1403 | 1407 | 1407 | 1407 |
|  | 4th | 1484 | 1381 | 1714 | 1637 |
|  | Mean | 1451 | 1407 | 1535 | 1503 |
|  | Standard deviation | 34 | 21 | 130 | 99 |
|  | Coefficient of variation | 2.4% | 1.5% | 8.5% | 6.6% |
| Column B | 1st | 1509 | 1407 | 1663 | 1688 |
|  | 2nd | 1535 | 1381 | 1612 | 1612 |
|  | 3rd | 1600 | 1415 | 1503 | 1509 |
|  | Mean | 1548 | 1401 | 1593 | 1603 |
|  | Standard deviation | 47 | 18 | 82 | 90 |
|  | Coefficient of variation | 3.0% | 1.3% | 5.1% | 5.6% |

Example 3 and Comparative Example 3

Separation of nucleic acid from a sample containing nucleic acid and measurement of the separated nucleic acid by a DNA microarray were carried out in the same manner as in Examples 1 and 2 except that guanidine thiocyanate was used instead of guanidine hydrochloride as the chaotropic agent, and that the nucleic acid purification columns A to F shown in Table 1 were used (Example 3).

As the solution containing the chaotropic agent, a solution of 2.1 M guanidine thiocyanate in 67% ethanol was used.

TABLE 3

| Chaotropic agent that was allowed to flow | | Example 3 Solution of 2.1M guanidine thiocyanate in 67% ethanol | Comparative Example 3 Sterile purified water |
|---|---|---|---|
| Column A | 1st | 1497 | 1629 |
|  | 2nd | 1467 | 1633 |
|  | 3rd | 1502 | 1473 |
|  | Mean | 1489 | 1578 |
|  | Standard deviation | 19 | 91 |
|  | Coefficient of variation | 1.3% | 5.8% |

TABLE 3-continued

| Chaotropic agent that was allowed to flow | | Example 3 Solution of 2.1M guanidine thiocyanate in 67% ethanol | Comparative Example 3 Sterile purified water |
|---|---|---|---|
| Column B | 1st | 1491 | 1523 |
| | 2nd | 1519 | 1610 |
| | 3rd | 1487 | 1450 |
| | Mean | 1499 | 1528 |
| | Standard deviation | 17 | 80 |
| | Coefficient of variation | 1.2% | 5.2% |
| Column C | 1st | 1479 | 1580 |
| | 2nd | 1512 | 1660 |
| | 3rd | 1459 | 1480 |
| | Mean | 1483 | 1573 |
| | Standard deviation | 27 | 90 |
| | Coefficient of variation | 1.8% | 5.7% |
| Column D | 1st | 1501 | 1440 |
| | 2nd | 1533 | 1593 |
| | 3rd | 1489 | 1603 |
| | Mean | 1508 | 1545 |
| | Standard deviation | 23 | 91 |
| | Coefficient of variation | 1.5% | 5.9% |
| Column E | 1st | 1479 | 1430 |
| | 2nd | 1498 | 1593 |
| | 3rd | 1445 | 1540 |
| | Mean | 1474 | 1521 |
| | Standard deviation | 27 | 83 |
| | Coefficient of variation | 1.8% | 5.5% |
| Column F | 1st | 1490 | 1450 |
| | 2nd | 1483 | 1550 |
| | 3rd | 1439 | 1632 |
| | Mean | 1471 | 1544 |
| | Standard deviation | 28 | 91 |
| | Coefficient of variation | 1.9% | 5.9% |

Example 4

Our nucleic acid purification column was prepared by a step of allowing a solution containing a chaotropic agent to flow through a nucleic acid-binding solid-phase carrier, and then drying the nucleic acid-binding solid-phase carrier.

As the nucleic acid-binding solid-phase carrier, a silica membrane (manufactured by Advantec Toyo Kaisha, Ltd.; model number, QR-100) was used. As a hollow body in which an inlet opening section and an outlet opening section are formed, a Micro Bio-Spin Chromatography Column (BioRad; model number, 7326204) was used.

The silica filter paper was cut out into a circular shape using a round punch having a diameter of 7 mm, and packed into the Micro Bio-Spin Chromatography Column. By fitting a polypropylene O-ring having a diameter of 7 mm thereon, the silica membrane was fixed to the column (hollow body). The step of passing the solution containing the chaotropic agent through the nucleic acid-binding solid-phase carrier was carried out by the following procedures. As the solution containing the chaotropic agent, 800 μL of a solution of 2.1 M guanidine thiocyanate in 67% ethanol was placed on the column, and then the column was centrifuged at 12,000×g for 1 minute to remove the solution. Subsequently, 800 μL of water was placed on the column, and then the column was centrifuged at 12,000×g for 1 minute to remove the water. Thereafter, the column was left to stand in a room for 6 hours to allow natural drying.

Our nucleic acid purification column (—"Column G") was thus prepared.

Example 5

Our nucleic acid purification columns were prepared by passing a solution containing a chaotropic agent through the nucleic acid purification columns A to F contained in the commercially available nucleic acid purification kits described in Table 1.

The step of passing the solution containing the chaotropic agent (including the water washing step) was carried out for Columns A to F by the procedures described in Example 3. After removing the solution by centrifugation, each column was left to stand in a room for 6 hours to allow natural drying.

Thus, our nucleic acid purification columns through which the solution containing guanidine thiocyanate as the chaotropic agent had been allowed to flow ("Column A'" to "Column F'," respectively) were prepared.

Example 6

In the same manner as in Examples 1 and 2, the Columns A' to F' prepared in Example 5 and the Column G prepared in Example 4 were used to separate nucleic acid from the prepared nucleic acid sample, and then the nucleic acid was measured using the DNA microarray. From the measured values, the standard deviation and the coefficient of variation of the number of detected miRNAs among the plurality of times of measurement were determined (Table 4).

As a result of the analysis, the coefficient of variation was found to be 1.2% to 1.7% in Columns A' to F', and 1.0% in Column G. Based on comparison with Comparative Example 3, in which sterile purified water was allowed to flow and the coefficient of variation was 5.2% to 5.9%, our nucleic acid purification columns were found to produce a measurement variation-reducing effect.

TABLE 4

| Chaotropic agent that was allowed to flow | | Example 3 Solution of 2.1M guanidine thiocyanate in 67% ethanol |
|---|---|---|
| Column A' | 1st | 1501 |
| | 2nd | 1477 |
| | 3rd | 1519 |
| | Mean | 1499 |
| | Standard deviation | 21 |
| | Coefficient of variation | 1.4% |
| Column B' | 1st | 1482 |
| | 2nd | 1522 |
| | 3rd | 1499 |
| | Mean | 1501 |
| | Standard deviation | 20 |
| | Coefficient of variation | 1.3% |
| Column C' | 1st | 1520 |
| | 2nd | 1477 |
| | 3rd | 1489 |
| | Mean | 1495 |
| | Standard deviation | 22 |
| | Coefficient of variation | 1.5% |
| Column D' | 1st | 1523 |
| | 2nd | 1510 |
| | 3rd | 1488 |
| | Mean | 1507 |
| | Standard deviation | 18 |
| | Coefficient of variation | 1.2% |
| Column E' | 1st | 1459 |
| | 2nd | 1501 |
| | 3rd | 1488 |
| | Mean | 1483 |
| | Standard deviation | 22 |
| | Coefficient of variation | 1.5% |
| Column F' | 1st | 1498 |
| | 2nd | 1450 |
| | 3rd | 1486 |
| | Mean | 1478 |
| | Standard deviation | 25 |
| | Coefficient of variation | 1.7% |

TABLE 4-continued

| Chaotropic agent that was allowed to flow | | Example 3 Solution of 2.1M guanidine thiocyanate in 67% ethanol |
|---|---|---|
| Column G | 1st | 1504 |
| | 2nd | 1479 |
| | 3rd | 1480 |
| | Mean | 1488 |
| | Standard deviation | 14 |
| | Coefficient of variation | 1.0% |

Examples 6 and 7, and Comparative Example 6

The commercially available nucleic acid purification columns A to F after allowing the solution of 2.1 M guanidine thiocyanate in 67% ethanol to flow therethrough in Example 3 (Example 6), and the Columns A' to F' prepared in Example 5 and the Column G prepared in Example 4 (Example 7), were subjected to detection of nucleic acid contained in an eluate obtained with sterile purified water to verify whether or not contamination with (residual) nucleic acid is found in each column. For comparison, the commercially available nucleic acid purification columns A to F after allowing sterile purified water to flow therethrough in Example 3 (Comparative Example 6) were similarly subjected to the measurement.

By adding 70 μL of sterile purified water dropwise to each column, and then centrifuging the column, an eluate was obtained. The nucleic acid contained in the eluate was measured by the same procedure as in Examples 1 and 2. Table 5 shows the number of detected miRNAs.

In the eluates from the Columns A to F after allowing sterile purified water to flow without allowing the solution containing the chaotropic agent to flow, 50 to 269 kinds of miRNAs were detected. On the other hand, in the Columns A to F after the treatment with the solution of 2.1 M guanidine thiocyanate in 67% ethanol, and the columns A' to F' and G produced by the process in which the chaotropic agent was allowed to flow, nucleic acid was hardly detected in the eluate. We thus found that all of the commercially available nucleic acid purification columns were contaminated with nucleic acid, and that the contaminant nucleic acid was removed by subjecting the commercially available nucleic acid purification columns to the process of allowing the chaotropic agent to flow by our method. We also found that our nucleic acid purification columns produced by the process in which the chaotropic agent was allowed to flow were not contaminated with nucleic acid.

TABLE 5

| Chaotropic agent that was allowed to flow | Comparative Example 6 Sterile purified water | Example 6 Solution of 2.1M guanidine thiocyanate in 67% ethanol | Chaotropic agent that was allowed to flow | Example 7 Solution of 2.1M guanidine thiocyanate in 67% ethanol |
|---|---|---|---|---|
| Column A | 248 | 0 | Column A' | 1 |
| Column B | 258 | 2 | Column B' | 0 |
| Column C | 269 | 1 | Column C' | 2 |
| Column D | 50 | 0 | Column D' | 2 |
| Column E | 124 | 4 | Column E' | 0 |
| Column F | 68 | 0 | Column F' | 5 |
| | | | Column G | 1 |

The invention claimed is:

1. A method of separating a nucleic acid from a sample containing the nucleic acid, the method comprising:
    (1) bringing the sample containing the target nucleic acid into contact with a nucleic acid-binding solid-phase carrier capable of adsorbing the nucleic acid; and
    (2) eluting the nucleic acid from the nucleic acid-binding solid-phase carrier to which the nucleic acid is adsorbed in the Step (1),
    wherein the nucleic acid-binding solid-phase carrier is brought into contact with a solution containing both a chaotropic agent and an alcohol before Step (1).

2. The method according to claim 1, further comprising washing the nucleic acid-binding solid-phase carrier with water or an aqueous alcohol solution after bringing the nucleic acid-binding solid-phase carrier into contact with the solution containing the chaotropic agent.

3. The method according to claim 1, wherein the nucleic acid-binding solid-phase carrier is a silica membrane.

4. The method according to claim 1, wherein the chaotropic agent is any of guanidinium salt, urea, iodide salt, chloric acid salt, perchloric acid salt, thiocyanic acid salt, and isothiocyanic acid salt.

5. The method according to claim 1, wherein the alcohol is ethanol.

6. The method according to claim 1, wherein the nucleic acid is DNA or RNA.

7. A method of detecting a nucleic acid, the method comprising:
    (1) bringing a sample containing the target nucleic acid into contact with a nucleic acid-binding solid-phase carrier capable of adsorbing the nucleic acid;
    (2) eluting the nucleic acid from the nucleic acid-binding solid-phase carrier to which the nucleic acid is adsorbed in (1); and
    (3) labeling and detecting the eluted nucleic acid,
    wherein the nucleic acid-binding solid-phase carrier is brought into contact with a solution containing both a chaotropic agent and an alcohol before (1).

8. A nucleic acid purification column comprising:
    a hollow body in which an inlet opening section and an outlet opening section are formed; and
    a nucleic acid-binding solid-phase carrier,
    which nucleic acid purification column is produced by a method comprising allowing a solution containing both a chaotropic agent and an alcohol to flow through the nucleic acid-binding solid-phase carrier, and then drying the nucleic acid-binding solid-phase carrier.

9. A method of producing a nucleic acid purification column, the column comprising:
    a hollow body in which an inlet opening section and an outlet opening section are formed; and
    a nucleic acid-binding solid-phase carrier, the method comprising:
    allowing a solution containing a chaotropic agent to flow through the nucleic acid-binding solid-phase carrier, and
    drying the nucleic acid-binding solid-phase carrier.

10. The method according to claim 9, further comprising washing the nucleic acid-binding solid-phase carrier with water or an aqueous alcohol solution after allowing the solution containing the chaotropic agent to flow through the nucleic acid-binding solid-phase carrier.

11. The method according to claim 9, wherein allowing the solution to flow is carried out in a state where the nucleic acid-binding solid-phase carrier is packed in the hollow body.

12. The method according to claim 9, wherein the nucleic acid-binding solid-phase carrier is a silica membrane.

13. The method according to claim 9, wherein the chaotropic agent is guanidinium salt, urea, iodide salt, chloric acid salt, perchloric acid salt, thiocyanic acid salt, or isothiocyanic acid salt.

* * * * *